United States Patent
An et al.

(10) Patent No.: US 7,763,581 B2
(45) Date of Patent: Jul. 27, 2010

(54) MUTANTS OF TRICHOSANTHIN WITH ANTI-TUMOR ACTIVITY AND LOWERED SIDE-EFFECTS

(76) Inventors: Chengcai An, No. 5, YiHeYuan Road, Beijing (CN) 100871; Shuangli Mi, No. 5, YiHeYuan Road, Beijing (CN) 100871; Ye Wang, No. 5, YiHeYuan Road, Beijing (CN) 100871; Yin Gao, No. 5, YiHeYuan Road, Beijing (CN) 100871

( * ) Notice: Subject to any disclaimer, the term of this patent is extended or adjusted under 35 U.S.C. 154(b) by 495 days.

(21) Appl. No.: 11/662,460

(22) PCT Filed: Aug. 4, 2005

(86) PCT No.: PCT/CN2005/001196

§ 371 (c)(1),
(2), (4) Date: Mar. 9, 2007

(87) PCT Pub. No.: WO2006/026906

PCT Pub. Date: Mar. 16, 2006

(65) Prior Publication Data

US 2008/0261874 A1    Oct. 23, 2008

(30) Foreign Application Priority Data

Sep. 9, 2004   (CN) .................... 2004 1 0074324

(51) Int. Cl.
*A61K 38/00*  (2006.01)
(52) U.S. Cl. .......................... 514/2; 530/350
(58) Field of Classification Search ............ 514/2; 530/350
See application file for complete search history.

(56) References Cited

FOREIGN PATENT DOCUMENTS

| WO | WO 90/12097 | 10/1990 |
|---|---|---|
| WO | WO 02/12537 A2 | 2/2002 |

OTHER PUBLICATIONS

Zips et al, 2005, In vivo, 19: 1-8.*
Lee et al, 1999, J Immunol, 163: 6292-6300.*
Kirkin et al, 1998, APMIS, 106 : 665-679.*
Mellman I, 2006, The Scientist, 20(1): 47-56.*
Kaiser (Science, 2006, 313, 1370).*
Bodey et al, 2000, Anticancer Res, 20: 2665-2676.*
Zhang et al, 2003, Talanta, 57(3): 467-73.*
Zhang F. Lu Y. J. Shaw P. C. Sui, S. F. Change in pH-dependent membrane insertion characteristics of trichosanthin caused by deletion of its last seven C-terminal amino acid residues. Biochemistry (Mosc),2003, 68(4):436-445.
Wang J. H., Nie H. L., Tam S. C., Huang H., Zheng Y. T. Anti-HIV-1 property of trichosanthin correlates with its ribosome inactivating activity. FEBS Lett, 2002, 531(2): 295-298.

* cited by examiner

*Primary Examiner*—Larry R. Helms
*Assistant Examiner*—Minh-Tam Davis
(74) *Attorney, Agent, or Firm*—Cohen Pontani Lieberman & Pavane LLP

(57) ABSTRACT

The invention provides the mutants and coding genes of trichosanthin (TCS). The mutants thereof are the TCS mutants with the single or double alternation of tyrosine-55 and aspartate-78 (counted from N-terminus), wherein the tyrosine-55 is mutated to an aliphatic amino acid and aspartate-78 is mutated to an amino acid with low hydrophilicity. This invention also relates to the application of TCS mutants and their coding genes in the drug development to treat carcinoma, AIDS and other diseases.

6 Claims, 3 Drawing Sheets

SEQUENCE LISTING

<160> NUMBER OF SEQ ID NOS: 16

<210> SEQ ID NO 1
<211> LENGTH: 741
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
gatgttagct tccggttatc aggtgcaaca agcagttcct atggagtttt catttcaaat    60
ctgagaaaag ctcttccaaa tgaaggaga ctatacgata tccctctgtt acgttccact   120
cttcaaggtt ctcaacgcta cgcattgatc catctcacaa atggcgccga tgaaaccatt   180
tcagtggcca tagacgtaac gaacgtctat attatgggat atcgcgctgg cgatacatcc   240
tattttttca acgaggcttc tgcaacagaa gctgcaaaat atgtattcaa agacgctatg   300
cgaaaagtta cgcttccata ttctggcaat tacgaaaggc ttcaaactgc tgcgggcaaa   360
ataagggaaa atattccgct tggactccca gctttggaca gtgccattac cactttgttt   420
tactacaacg ccaattctgc tgcgtcggca cttatggtac tcattcagtc gacgtctgag   480
gctgcgaggt ataaatttat tgagcaacaa attgggaagc gcgctgacaa aaccttccta   540
ccaagtttag caattataag tttggaaaat agttggtctg ctctctccaa gcaaattcag   600
atagcgagta ctaataatgg acagtttgaa actcctgttg tgcttataaa tgctcaaaac   660
caacgagtcg cgataaccaa tgttgatgct ggagttgtaa cctccaacat cgcgttgctg   720
ctgaatcgaa acaatatggc a                                              741
```

<210> SEQ ID NO 2
<211> LENGTH: 741
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
gatgttagct tccggttatc aggtgcaaca agcagttcct atggagtttt catttcaaat    60
ctgagaaaag ctcttccaaa tgaaggaga ctatacgata tccctctgtt acgttccact   120
cttcaaggtt ctcaacgcta cgcattgatc catctcacaa attacgccga tgaaaccatt   180
tcagtggcca tagacgtaac gaacgtctat attatgggat atcgcgctgg ctccacatcc   240
tattttttca acgaggcttc tgcaacagaa gctgcaaaat atgtattcaa agacgctatg   300
cgaaaagtta cgcttccata ttctggcaat tacgaaaggc ttcaaactgc tgcgggcaaa   360
ataagggaaa atattccgct tggactccca gctttggaca gtgccattac cactttgttt   420
tactacaacg ccaattctgc tgcgtcggca cttatggtac tcattcagtc gacgtctgag   480
gctgcgaggt ataaatttat tgagcaacaa attgggaagc gcgctgacaa aaccttccta   540
ccaagtttag caattataag tttggaaaat agttggtctg ctctctccaa gcaaattcag   600
atagcgagta ctaataatgg acagtttgaa actcctgttg tgcttataaa tgctcaaaac   660
caacgagtcg cgataaccaa tgttgatgct ggagttgtaa cctccaacat cgcgttgctg   720
ctgaatcgaa acaatatggc a                                              741
```

-continued

```
<210> SEQ ID NO 3
<211> LENGTH: 741
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gatgttagct tccggttatc aggtgcaaca agcagttcct atggagtttt catttcaaat    60
ctgagaaaag ctcttccaaa tgaaaggaga ctatacgata tccctctgtt acgttccact   120
cttcaaggtt ctcaacgcta cgcattgatc catctcacaa atggcgccga tgaaaccatt   180
tcagtggcca tagacgtaac gaacgtctat attatgggat atcgcgctgg ctccacatcc   240
tattttttca acgaggcttc tgcaacagaa gctgcaaaat atgtattcaa agacgctatg   300
cgaaaagtta cgcttccata ttctggcaat tacgaaaggc ttcaaactgc tgcgggcaaa   360
ataaggggaa atattccgct tggactccca gctttggaca gtgccattac cactttgttt   420
tactacaacg ccaattctgc tgcgtcggca cttatggtac tcattcagtc gacgtctgag   480
gctgcgaggt ataaatttat tgagcaacaa attgggaagc gcgctgacaa aaccttccta   540
ccaagtttag caattataag tttggaaaat agttggtctg ctctctccaa gcaaattcag   600
atagcgagta ctaataatgg acagtttgaa actcctgttg tgcttataaa tgctcaaaac   660
caacgagtcg cgataaccaa tgttgatgct ggagttgtaa cctccaacat cgcgttgctg   720
ctgaatcgaa acaatatggc a                                            741

<210> SEQ ID NO 4
<211> LENGTH: 741
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
gatgttagct tccggttatc aggtgcaaca agcagttcct atggagtttt catttcaaat    60
ctgagaaaag ctcttccaaa tgaaaggaga ctatacgata tccctctgtt acgttccact   120
cttcaaggtt ctcaacgcta cgcattgatc catctcacaa attacgccga tgaaaccatt   180
tcagtggcca tagacgtaac gaacgtctat attatgggat atcgcgctgg cgatacatcc   240
tattttttca acgaggcttc tgcaacagaa gctgcaaaat atgtattcaa agacgctatg   300
cgaaaagtta cgcttccata ttctggcaat tacgaaaggc ttcaaactgc tgcgggcaaa   360
ataaggggaa atattccgct tggactccca gctttggaca gtgccattac cactttgttt   420
tactacaacg ccaattctgc tgcgtcggca cttatggtac tcattcagtc gacgtctgag   480
gctgcgaggt ataaatttat tgagcaacaa attgggaagc gcgctgacaa aaccttccta   540
ccaagtttag caattataag tttggaaaat agttggtctg ctctctccaa gcaaattcag   600
atagcgagta ctaataatgg acagtttgaa actcctgttg tgcttataaa tgctcaaaac   660
caacgagtcg cgataaccaa tgttgatgct ggagttgtaa cctccaacat cgcgttgctg   720
ctgaatcgaa acaatatggc a                                            741

<210> SEQ ID NO 5
<211> LENGTH: 247
<212> TYPE: PRT
<213> ORGANISM: Artificial Sequence
<220> FEATURE:
```

-continued

<223> OTHER INFORMATION: Description of Artificial Sequence: Synthetic
      polypeptide

<400> SEQUENCE: 5

Asp Val Ser Phe Arg Leu Ser Gly Ala Thr Ser Ser Ser Tyr Gly Val
1               5                   10                  15

Phe Ile Ser Asn Leu Arg Lys Ala Leu Pro Asn Glu Arg Arg Leu Tyr
            20                  25                  30

Asp Ile Pro Leu Leu Arg Ser Thr Leu Gln Gly Ser Gln Arg Tyr Ala
        35                  40                  45

Leu Ile His Leu Thr Asn Gly Ala Asp Glu Thr Ile Ser Val Ala Ile
    50                  55                  60

Asp Val Thr Asn Val Tyr Ile Met Gly Tyr Arg Ala Gly Asp Thr Ser
65                  70                  75                  80

Tyr Phe Phe Asn Glu Ala Ser Ala Thr Glu Ala Ala Lys Tyr Val Phe
                85                  90                  95

Lys Asp Ala Met Arg Lys Val Thr Leu Pro Tyr Ser Gly Asn Tyr Glu
            100                 105                 110

Arg Leu Gln Thr Ala Ala Gly Lys Ile Arg Glu Asn Ile Pro Leu Gly
        115                 120                 125

Leu Pro Ala Leu Asp Ser Ala Ile Thr Thr Leu Phe Tyr Tyr Asn Ala
    130                 135                 140

Asn Ser Ala Ala Ser Ala Leu Met Val Leu Ile Gln Ser Thr Ser Glu
145                 150                 155                 160

Ala Ala Arg Tyr Lys Phe Ile Glu Gln Gln Ile Gly Lys Arg Ala Asp
                165                 170                 175

Lys Thr Phe Leu Pro Ser Leu Ala Ile Ile Ser Leu Glu Asn Ser Trp
            180                 185                 190

Ser Ala Leu Ser Lys Gln Ile Gln Ile Ala Ser Thr Asn Asn Gly Gln
        195                 200                 205

Phe Glu Thr Pro Val Val Leu Ile Asn Ala Gln Asn Gln Arg Val Ala
    210                 215                 220

Ile Thr Asn Val Asp Ala Gly Val Val Thr Ser Asn Ile Ala Leu Leu
225                 230                 235                 240

Leu Asn Arg Asn Asn Met Ala
                245

<210> SEQ ID NO 6
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Val Ser Phe Arg Leu Ser Gly Ala Thr Ser Ser Ser Tyr Gly Val
1               5                   10                  15

Phe Ile Ser Asn Leu Arg Lys Ala Leu Pro Asn Glu Arg Arg Leu Tyr
            20                  25                  30

Asp Ile Pro Leu Leu Arg Ser Thr Leu Gln Gly Ser Gln Arg Tyr Ala
        35                  40                  45

Leu Ile His Leu Thr Asn Tyr Ala Asp Glu Thr Ile Ser Val Ala Ile
    50                  55                  60

Asp Val Thr Asn Val Tyr Ile Met Gly Tyr Arg Ala Gly Ser Thr Ser
65                  70                  75                  80

```
Tyr Phe Phe Asn Glu Ala Ser Ala Thr Glu Ala Ala Lys Tyr Val Phe
                 85                  90                  95

Lys Asp Ala Met Arg Lys Val Thr Leu Pro Tyr Ser Gly Asn Tyr Glu
            100                 105                 110

Arg Leu Gln Thr Ala Ala Gly Lys Ile Arg Glu Asn Ile Pro Leu Gly
        115                 120                 125

Leu Pro Ala Leu Asp Ser Ala Ile Thr Thr Leu Phe Tyr Tyr Asn Ala
130                 135                 140

Asn Ser Ala Ala Ser Ala Leu Met Val Leu Ile Gln Ser Thr Ser Glu
145                 150                 155                 160

Ala Ala Arg Tyr Lys Phe Ile Glu Gln Gln Ile Gly Lys Arg Ala Asp
                165                 170                 175

Lys Thr Phe Leu Pro Ser Leu Ala Ile Ile Ser Leu Glu Asn Ser Trp
            180                 185                 190

Ser Ala Leu Ser Lys Gln Ile Gln Ile Ala Ser Thr Asn Asn Gly Gln
        195                 200                 205

Phe Glu Thr Pro Val Val Leu Ile Asn Ala Gln Asn Gln Arg Val Ala
210                 215                 220

Ile Thr Asn Val Asp Ala Gly Val Val Thr Ser Asn Ile Ala Leu Leu
225                 230                 235                 240

Leu Asn Arg Asn Asn Met Ala
            245
```

<210> SEQ ID NO 7
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Asp Val Ser Phe Arg Leu Ser Gly Ala Thr Ser Ser Tyr Gly Val
  1               5                  10                  15

Phe Ile Ser Asn Leu Arg Lys Ala Leu Pro Asn Glu Arg Arg Leu Tyr
                 20                  25                  30

Asp Ile Pro Leu Leu Arg Ser Thr Leu Gln Gly Ser Gln Arg Tyr Ala
            35                  40                  45

Leu Ile His Leu Thr Asn Gly Ala Asp Glu Thr Ile Ser Val Ala Ile
        50                  55                  60

Asp Val Thr Asn Val Tyr Ile Met Gly Tyr Arg Ala Gly Ser Thr Ser
65                  70                  75                  80

Tyr Phe Phe Asn Glu Ala Ser Ala Thr Glu Ala Ala Lys Tyr Val Phe
                 85                  90                  95

Lys Asp Ala Met Arg Lys Val Thr Leu Pro Tyr Ser Gly Asn Tyr Glu
            100                 105                 110

Arg Leu Gln Thr Ala Ala Gly Lys Ile Arg Glu Asn Ile Pro Leu Gly
        115                 120                 125

Leu Pro Ala Leu Asp Ser Ala Ile Thr Thr Leu Phe Tyr Tyr Asn Ala
130                 135                 140

Asn Ser Ala Ala Ser Ala Leu Met Val Leu Ile Gln Ser Thr Ser Glu
145                 150                 155                 160

Ala Ala Arg Tyr Lys Phe Ile Glu Gln Gln Ile Gly Lys Arg Ala Asp
                165                 170                 175

Lys Thr Phe Leu Pro Ser Leu Ala Ile Ile Ser Leu Glu Asn Ser Trp
            180                 185                 190
```

Ser Ala Leu Ser Lys Gln Ile Gln Ile Ala Ser Thr Asn Asn Gly Gln
          195                 200                 205

Phe Glu Thr Pro Val Val Leu Ile Asn Ala Gln Asn Gln Arg Val Ala
          210                 215                 220

Ile Thr Asn Val Asp Ala Gly Val Val Thr Ser Asn Ile Ala Leu Leu
225                 230                 235                 240

Leu Asn Arg Asn Asn Met Ala
              245

<210> SEQ ID NO 8
<211> LENGTH: 247
<212> TYPE: PRT
<213> ORGANISM: Trichosanthes kirilowii

<400> SEQUENCE: 8

Asp Val Ser Phe Arg Leu Ser Gly Ala Thr Ser Ser Ser Tyr Gly Val
1               5                   10                  15

Phe Ile Ser Asn Leu Arg Lys Ala Leu Pro Asn Glu Arg Arg Leu Tyr
            20                  25                  30

Asp Ile Pro Leu Leu Arg Ser Thr Leu Gln Gly Ser Gln Arg Tyr Ala
        35                  40                  45

Leu Ile His Leu Thr Asn Tyr Ala Asp Glu Thr Ile Ser Val Ala Ile
    50                  55                  60

Asp Val Thr Asn Val Tyr Ile Met Gly Tyr Arg Ala Gly Asp Thr Ser
65                  70                  75                  80

Tyr Phe Phe Asn Glu Ala Ser Ala Thr Glu Ala Ala Lys Tyr Val Phe
                85                  90                  95

Lys Asp Ala Met Arg Lys Val Thr Leu Pro Tyr Ser Gly Asn Tyr Glu
            100                 105                 110

Arg Leu Gln Thr Ala Ala Gly Lys Ile Arg Glu Asn Ile Pro Leu Gly
        115                 120                 125

Leu Pro Ala Leu Asp Ser Ala Ile Thr Thr Leu Phe Tyr Tyr Asn Ala
130                 135                 140

Asn Ser Ala Ala Ser Ala Leu Met Val Leu Ile Gln Ser Thr Ser Glu
145                 150                 155                 160

Ala Ala Arg Tyr Lys Phe Ile Glu Gln Gln Ile Gly Lys Arg Ala Asp
                165                 170                 175

Lys Thr Phe Leu Pro Ser Leu Ala Ile Ile Ser Leu Glu Asn Ser Trp
            180                 185                 190

Ser Ala Leu Ser Lys Gln Ile Gln Ile Ala Ser Thr Asn Asn Gly Gln
          195                 200                 205

Phe Glu Thr Pro Val Val Leu Ile Asn Ala Gln Asn Gln Arg Val Ala
          210                 215                 220

Ile Thr Asn Val Asp Ala Gly Val Val Thr Ser Asn Ile Ala Leu Leu
225                 230                 235                 240

Leu Asn Arg Asn Asn Met Ala
              245

<210> SEQ ID NO 9
<211> LENGTH: 4
<212> TYPE: PRT
<213> ORGANISM: Trichosanthes kirilowii

<400> SEQUENCE: 9

Lys Ile Arg Glu
 1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Ala Gly Gly
  1

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggcatcatat ggatgttagc ttccggtta                                      29

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gggaagctta tgccatattg tttcgatt                                       28

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
catcggcgcc atttgtgag                                                 19

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctcacaaatg gcgccgatg                                                 19

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aggatgtgga gccagcgcg                                                 19

```
<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cgcgctggct ccacatcct                                                    19
```

MUTANTS OF TRICHOSANTHIN WITH ANTI-TUMOR ACTIVITY AND LOWERED SIDE-EFFECTS

PRIORITY CLAIM

This is a U.S. national stage of application No. PCT/CN2005/001196, filed on Aug. 4, 2005. Priority is claimed on the following application(s): Country: China, Application No.: 200410074324.6, Filed: Sep. 9, 2004 the content of which is incorporated here by reference.

TECHNICAL FIELD

The invention relates to the mutant genes and proteins of trichosanthin in the field of genetic engineering. More specifically, the invention relates to the application of these genes and proteins in the drug production to treat carcinoma, AIDS and other diseases.

TECHNICAL BACKGROUND

Trichosanthin (TCS) is the active gradient of Chinese traditional medicine TIANHUAFEN, which is isolated from the root tuber of liana *Trichosanthes kirilowii* Maxim. TCS possesses multiple biological activities including abortifacient, immunoregulation, anti-tumor, and antiviral functions. In clinic, TCS exhibits significant effects on the treatment of abnormal proliferation of cytotrophoblast cells, such as hydatidiform mole, malignant hydatidiform mole and choriocarcinoma. In 1989, the discovery of the anti-HIV activity of TCS drew attentions worldwide.

TCS (GeneBank Accession number AY669811, SEQ ID NO: 8) comprises 247 amino acids with the molecular weight of about 27 kD and the pI of 9.4. It is a simple protein, without any glycosylation or other modifications. TCS belongs to type-I ribosome-inactivating proteins (RIPs) that can inhibit protein translation by specifically hydrolyzing the N—C glycosidic bond at 4324-adenosine of ribosomal 28S RNA of eukaryote. TCS can break supercoiled DNA and induce tumor cell apoptosis in vitro via caspase pathway. The main reason for TCS to kill tumor cells is the ribosome-inactivating and apoptosis-inducing activities.

It is believed that only after entering into target cells, can TCS play cytotoxic function, but the pathway by which type-I RIPs entering into cells is not clear. Recently, it was reported that the LDL-receptor family members played important roles in the cell entry of TCS, but the critical domain in TCS molecule interacting with its receptor is still undiscovered.

The future of TCS in clinical application is promising because of its medicinal value. However, as a protein derived from plant, the immunogenicity and side-effects of TCS are serious. Its clinical responses, including fever, urticaria, edema, muscle pains, and even effects on nerve centre, limit the application of TCS.

The side-effects of TCS come from two aspects. One is the immunogenecity of the epitopes on the surface of TCS molecule, and the other is the cytotoxicity on normal cells after TCS enters tissue cells. To decrease the side-effects of TCS, two considerations are proven to be effective: a) to remove the epitopes of TCS; and b) to change the cell entry of TCS by modifying the critical sites for TCS cell entry. Because TCS has several widely distributed epitopes, it is difficult to remove all of them. In contrast, the modification on the key sites of TCS cell entry can make TCS enter target tumor cells specifically without entering into normal tissue cells, so as to decrease the side-effects of TCS and immunogenecity by affecting antigen presentation of antigen presenting cells.

Currently, most researches on TCS are focusing on the relationship between TCS structure and activities. Researches on the side-effects and immunogenecity of TCS, especially on the cell identification and TCS entry, however, are rarely reported.

In 2002, Wang J H et al. reported that two TCS mutants, Lys120-Ile121-Arg122-Glu123 (SEQ ID NO: 9) to Ser120-Ala121-Gly122-Gly123 (SEQ ID NO: 10) and TCSE160A/E189A, showed much lowered ribosome inactivating (RI) activity and loss of anti-HIV activity. The mutant of R122G showed anti-HIV activity but its RI activity decreased 160 times. In 2003, Zhang F et al. reported that the deletion of 7 residues on the C-terminus of TCS decreased the cytotoxicity in vivo and RI activity in vitro, with RI activity decreased to a greater extent.

At present, targeting drugs show great potential in the clinical treatment of carcinoma and other diseases. The targeting drugs are composed of a targeting moiety that is generally a monoclonal antibody or antibody fragment (e.g. ScFv) specifically against tumor cells or virus-infected cells, and a toxin moiety that has anti-tumor or antiviral activity. The targeting moiety and toxin are ligated by chemical couplers or gene-fusion to produce targeting drugs with specific anti-tumor or anti-virus roles.

SUMMARY OF THE INVENTION

One object of this invention is to provide the mutants of trichosanthin and their coding genes.

Another object of this invention is to provide the application of TCS mutants and their coding genes in the preparation of a medicament treating carcinoma, AIDS and other diseases. In one embodiment, the carcinoma is choriocarcinoma.

The TCS mutants provided in this invention refers to proteins in which at least one or both of tyrosine-55 (counted from N-terminus) and aspartate-78 (counted from N-terminus) are mutated, wherein tyrosine-55 is mutated to aliphatic amino acids and aspartate-78 is mutated to amino acids with low hydrophilicity.

In one aspect, the tyrosine is an aromatic amino acid, and the aspartate is an amino acid with high hydrophilicity.

The aliphatic amino acids mentioned above include glycine, alanine, valine, leucine, and isoleucine, wherein glycine is preferred. The amino acids with low hydrophilicity mentioned above include serine, threonine, asparagine, glutamine, alanine, and cysteine, wherein serine is preferred.

The coding genes of above-mentioned TCS mutants are also within the protection scope of this invention.

When the tyrosine-55 of the mutant (counted from the N-terminus of TCS) is mutated to glycine (this mutant is named as TCS$_{Y55G}$, with the amino acid sequence of SEQ ID No. 5), its coding gene (named as tcs$_{Y55G}$) has the nucleotide sequence of SEQ ID NO: 1 listed in the Sequence Listing; except the codon of glycine-55 (counted from N-terminus) can be GGC (163-165 counted from 5'-terminus of sequence 1 in the Sequence Listing) and other degenerate codons including GGA, GGT and GGG.

When the tyrosine-55 of the mutant (counted from the N-terminus of TCS) is mutated to alanine (this mutant is named as TCS$_{Y55A}$), its coding gene (named as tcs$_{Y55A}$) has the nucleotide sequence of SEQ ID NO: 1 listed in the Sequence Listing, except the 163-165 nucleotides (counted from 5'-terminus of sequence 1 in the Sequence Listing) are GCA, GCT, GCC or GCG that are codons of alanine.

When the tyrosine-55 of the mutant (counted from the N-terminus of TCS) is mutated to valine (this mutant is named as $TCS_{Y55A}$), its coding gene (named as $tcs_{Y55A}$) has the nucleotide sequence of SEQ ID NO: 1 listed in the Sequence Listing, except the 163-165 nucleotides (counted from 5'-terminus of sequence 1 in the Sequence Listing) are GTA, GTT, GTC or GTG that are codons of valine.

When the tyrosine-55 of the mutant (counted from the N-terminus of TCS) is mutated to leucine (this mutant is named as $TCS_{Y55L}$), its coding gene (named as $tcs_{Y55L}$) has the nucleotide sequence of SEQ ID NO: 1 listed in the Sequence Listing and the 163-165 nucleotides (counted from 5'-terminus of sequence 1 in the Sequence Listing) are CTA, CTT, CTC, CTG, TTA or TTG that are codons of leucine.

When the tyrosine-55 of the mutant (counted from the N-terminus of TCS) is mutated to isoleucine (this mutant is named as $TCS_{Y55I}$), its coding gene (named as $tcs_{Y55I}$) has the nucleotide sequence of SEQ ID NO: 1 listed in the Sequence Listing and the 163-165 nucleotides (counted from 5'-terminus of sequence 1 in the Sequence Listing) are ATT, ATC, or ATA that are codons of isoleucine.

When the aspartate-78 of the mutant (counted from the N-terminus of TCS) is mutated to serine (this mutant is named as $TCS_{D78S}$, with the amino acid sequence of SEQ ID No. 6), its coding gene (named as $tcs_{D78S}$) has the nucleotide sequence of SEQ ID NO: 2 listed in the Sequence Listing, except the 232-234 nucleotides (counted from 5'-terminus of sequence 2 in Sequence Listing) are TCC, TCA, TCT, TCG, AGT or AGC that are codons of serine.

When the aspartate-78 of the mutant (counted from the N-terminus of TCS) is mutated to threonine (this mutant is named as $TCS_{D78T}$), its coding gene (named as $tcs_{D78T}$) has the nucleotide sequence of SEQ ID NO: 2 listed in the Sequence Listing, except the 232-234 nucleotides (counted from 5'-terminus of sequence 2 in Sequence Listing) are ACA, ACT, ACC, or ACG that are codons of threonine.

When the aspartate-78 of the mutant (counted from the N-terminus of TCS) is mutated to asparagine (this mutant is named as $TCS_{D78N}$), its coding gene (named as $tcs_{D78N}$) has the nucleotide sequence of SEQ ID NO: 2 listed in the Sequence Listing, except the 232-234 nucleotides (counted from 5'-terminus of sequence 2 in Sequence Listing) are AAT or AAC that are codons of asparagine.

When the aspartate-78 of the mutant (counted from the N-terminus of TCS) is mutated to glutamine (this mutant is named as $TCS_{D78Q}$), its coding gene (named as $tcs_{D78Q}$) has the nucleotide sequence of SEQ ID NO: 2 listed in the Sequence Listing, except the 232-234 nucleotides (counted from 5'-terminus of sequence 2 in Sequence Listing) are CAA or CAG that are codons of glutamine.

When the aspartate-78 of the mutant (counted from the N-terminus of TCS) is mutated to alanine (this mutant is named as $TCS_{D78A}$), its coding gene (named as $tcs_{D78A}$) has the nucleotide sequence of SEQ ID NO: 2 listed in the Sequence Listing, except the 232-234 nucleotides (counted from 5'-terminus of sequence 2 in Sequence Listing) are GCA, GCT, GCC or GCG that are codons of alanine.

When the aspartate-78 of the mutant (counted from the N-terminus of TCS) is mutated to cysteine (this mutant is named as $TCS_{D78C}$), its coding gene (named as $tcs_{D78C}$) has the nucleotide sequence of SEQ ID NO: 2 listed in the Sequence Listing and the 232-234 nucleotides (counted from 5'-terminus of sequence 2 in Sequence Listing) are TGT or TGC that are codons of cysteine.

When the tyrosine-55 of the mutant (counted from the N-terminus of TCS) is mutated to glycine and simultaneously the aspartate-78 (counted from the N-terminus of TCS) is mutated to serine (this mutant is named as $TCS_{Y55G/D78S}$, SEQ ID NO:7), its coding gene (named as $tcs_{Y55G/D78S}$) has the nucleotide sequence of SEQ ID NO: 3 in the Sequence Listing. The 163-165 nucleotides (counted from 5'-terminus of sequence 3 in Sequence Listing) can be GGC or other degenerate condons including GGA, GGT and GGG, and the 232-234 nucleotides (counted from 5'-terminus of sequence 3 in Sequence Listing) can be TCC or other degenerate codons including TCA, TCT, TCG, AGT or AGC.

When the tyrosine-55 of the mutant (counted from the N-terminus of TCS) is mutated to alanine, valine, leucine or isoleucine, and simultaneously the aspartate-78 (counted from the N-terminus of TCS) is mutated to threonine, asparagine, glutamine, alanine or cysteine, the coding gene of this mutant has one of the following sequences:

1) the 163-165 nucleotides of SEQ ID NO: 3 (counted from 5'-terminus of sequence 3) are one of the following codons: GCA, GCT, GCC, GCG (encoding alanine); GTA, GTT, GTC, GTG (encoding valine); CTA, CTT, CTC, CTQ TTA, TTG (encoding leucine); ATT, ATC, ATA (encoding isoleucine);

2) the 232-234 nucleotides of SEQ ID NO: 3 (counted from 5'-terminus of sequence 3) are one of the following codons: ACA, ACT, ACC, ACG (encoding threonine); AAT, AAC (encoding asparagines); CAA, CAG (encoding glutamine); GCA, GCT, GCC, GCG (encoding alanine); TGT, TGC (encoding cysteine);

3) the 163-165 nucleotides of SEQ ID NO: 3 (counted from 5'-terminus of sequence 3) are one of the following codons: GGA, GGT, GGG, or GCA, GCT, GCC, GCG (encoding alanine); GTA, GTT, GTC, GTG (encoding valine); CTA, CTT, CTC, CTG, TTA, TTG (encoding leucine); ATT, ATC, ATA (encoding isoleucine); and simultaneously, the 232-234 nucleotides of Sequence 3 (counted from 5'-terminus of sequence 3) are one of the following codons: TCA, TCT, TCG, AGT, AGC or ACA, ACT, ACC, ACG (encoding threonine); AAT, AAC (encoding asparagines); CAA, CAG (encoding glutamine); GCA, GCT, GCC, GCG (encoding alanine); TGT, TGC (encoding cysteine).

This invention confirms the critical amino acids for TCS cell identification and entry into target cells—human choriocarcinoma (JAR) cells—are tyrosine-55 and aspartate-78. By using site-directed gene mutation, these two residues are altered and the mutants thereof lose the ability to enter cells and show decreased side-effects, but their other activities including anti-tumor function are maintained. Among these mutants, $TCS_{Y55G}$, $TCS_{D78S}$ and $TCS_{Y55G/D78S}$ are preferred.

Our evidences proved that the TCS mutants including $TCS_{Y55G}$, $TCS_{D78S}$ and $TCS_{Y55G/D78S}$ maintain the RI and protein synthesis inhibition activities in vitro, and maintain the ability to induce the caspase activation and cell apoptosis in cells, but loss the ability of entry into target cells, and especially decrease their immunogenecity and side-effects. These mutants have great potential as immunotoxin. The alterations on these two residues have no effect on its pharmaceutical functions, but only loss its cell entry ability. As a result, these mutants show no cytotoxicity on normal tissue cells and therefore have great potential to act as the toxin moiety in targeting drugs.

The mutants of the present invention have the advantages/properties of easy to prepare, high yields, easy to purify, and high solubility. All the mutants have RI and apoptosis-inducing activities but lose the ability of cell entry and decrease the side-effects on normal cells as well as immunogenecity. The mutants in this invention can play important roles in the clinical treatment of carcinoma, AIDS and other serious diseases.

DETAILED DESCRIPTION OF THE PRESENTLY PREFERRED EMBODIMENTS

Figure 1:
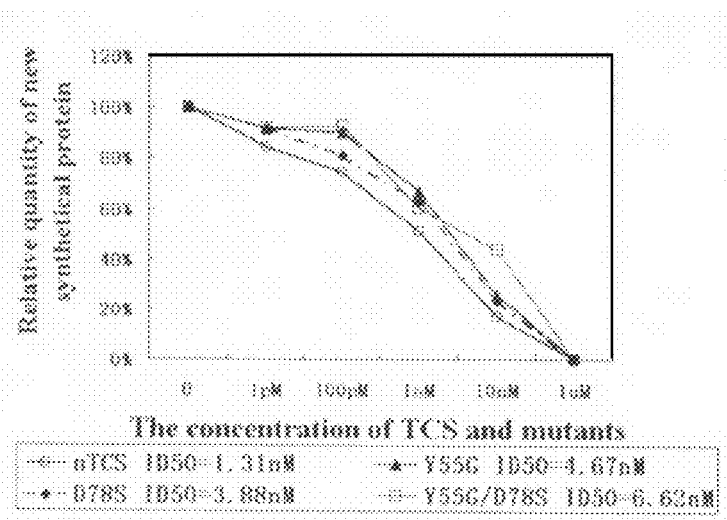
FIG. 1 is the RI activity curve of the TCS mutants $TCS_{Y55G}$, $TCS_{D78S}$ and $TCS_{Y55G/D78S}$.

The invention will be described in detail combined with the figures as follows, nevertheless, the invention is not intended to be limited to the following disclosure.

Example 1

The Expression and Purification of TCS Mutants

Based on the gene and amino acid sequence of mature TCS, as well as their tertiary structure analysis, the residues of tyrosine-55 and aspartate-78 are considered to be mutated. Using the target cells—JAR cells (ATC HTB-144), the residues of tyrosine-55 and aspartate-78 are considered to be the critical residues for TCS cell identification and cell entry.

Using the method of site-directed gene mutation, the tyrosine-55 of mature TCS is mutated to glycine, alanine, valine, leucine, or isoleucine; the aspartate-78 is mutated to serine, threonine, asparagine, glutamine, alanine, or cysteine; or both tyrosine-55 and aspartate-78 are mutated, the resultant mutants including $tcs_{Y55G}$, $tcs_{D78S}$ and $tcs_{Y55G/D78S}$. In the experiments, wide type tsc is used as the template for site-directed mutation PCR (sequenceSequence ID NO:4 in Sequence Listing); the reaction systems and cycle programs used in PCR are as follows:

Reaction System:

| | |
|---|---|
| $H_2O$ | 39 μl |
| dNTP | 2 μl |
| Forward primer | 1 μl |
| Reversed primer | 1 μl |
| Template | 1 μl |
| 10X Taq reaction buffer | 1 μl |
| Taq polymerase | 1 μl |
| Total volume | 50 μl |

Cycle Program:

| | | |
|---|---|---|
| Initial denaturation | 94° C. | 60 s |
| Denaturation | 94° C. | 60 s |
| Annealing | 58° C. | 70 s |
| Extension | 72° C. | 60 s |
| Cycle number | 35 cycles | |
| Final extension | 72° C. | 600 s |

Using the regular methods of molecular cloning, the above-mentioned mutant genes are cloned into expression vector pT7-7 (Sagon Co., Shanghai, China) between NdeI and HindIII, and then the recombinant plasmid is transformed into *E. coli* BL21 (DE3). After a single colony is cultured in LB medium at 37° C. for 12 hours, the bacteria is transplanted into fresh LB medium with a ratio of 1:100. When the OD600 of culture reaches 0.6-0.8, the gene is expressed with the induction of 0.5 mol/L IPTG. After cultured for 6-8 hours, the bacteria is collected and ultrasonically disrupted. The mutant proteins are purified by CM-Sepharose Fast Flow Chromatography. The purities of purified proteins reached 99%, determined by SDS-PAGE and Western blotting. The yields can be up to 13-14 mg/Liter culture.

In order to fuse the 5'-terminus of the mutant genes to Ndel site of pT7-7, the restriction site of Ndel CATATG is designed into PCR primer; in order to fuse the 3'-terminus of the mutant genes to HindIll site of pT7-7, the restriction site of HindIll, AAGCTT, and a stop codon TAA are both designed into PCR primer. The primers are as follows:

```
Primer 1:
5'-GGCATCATATGGATGTTAGCTTCCGGTTA-3';
(SEQ ID NO: 11)

Primer 2:
5'-GGGAAGCTTATGCCATATTGTTTCGATT-3';
(SEQ ID NO: 12)

Primer 3:
5'-CATCGGCGCCATTTGTGAG-3'
(SEQ ID NO: 13) (the italic bases encode glycine);
```

(For other 55-site mutants, the italic bases in primer 3 are replaced by CCT, CCA or CCC (encoding glycine); CGT, CGA, CGG, or CGC (encoding alanine); CAT, CM, CAG or CAC (encoding valnine); GAT, GAA, GAG, GAC, AAT or AAC (encoding leucine); TAA, TAG or TAT (encoding isoleucine).)

```
Primer 4:
5'-CTCACAAATGGCGCCGATG -3'
(SEQ ID NO: 14) (the italic bases encode glycine);
```

(For other 55-site mutants, the italic bases in primer 4 are replaced by GGA, GGT, or GGG (encoding glycine); GCA, GCT, GCC, or GCG (encoding alanine); GTA, GTT, GTC or GTG (encoding valnine); CTA, CTT, CTC, CTG, TTA or TTG (encoding leucine); ATT, ATC or ATA (encoding isoleucine).)

```
Primer 5:
5'-AGGATGTGGAGCCAGCGCG-3'
(SEQ ID NO: 15) (the italic bases encode serine);
```

(For other 78-site mutants, the italic bases in primer 5 are replaced by AGT, AGA, AGC, TCA or TCG (encoding serine); TAT, TGA, TGG, TGC (encoding threonine); TTA or TTG (encoding asparagine); GTT or GTC (encoding glutamine); CGT, CGA, CGG or CGC (encoding alanine); ACA or ACG (encoding cysteine).)

Primer 6:
5'-CGCGCTGG*CTCC*ACATCCT-3'
(SEQ ID NO: 16) (the italic bases encode serine);

(For other 78-site mutants, the italic bases in primer 5 are replaced by TCA, TCT, TCG, AGT, or AGC (encoding serine); ACA, ACT, ACC or ACG (encoding threonine); AAT or AAC (encoding asparagine); CAA or CAG (encoding glutamine); GCA, GCT, GCC, or GCG (encoding alanine); TGT or TGC (encoding cysteine).)

The detailed protocol to prepare $tcs_{Y55G}$, $tcs_{D78S}$ and $tcs_{Y55G/D78S}$ are as follows:

Preparing $tcs_{Y55G}$: the first round of PCR: the sequence of the template is given as SEQ ID NO: 4 in Sequence Listing, and primer 1 & 3 are used to produce fragment of tcs55-a; the second round of PCR: the sequence of the template is given as SEQ ID NO: 4 in Sequence Listing, and primer 2 & 4 are used to produce fragment of tcs55-b; the third round of PCR: the 1:1 mixture of tcs55-a and tcs55-b is used as PCR template, and primer 1 & 2 are used to produce $tcs_{Y55G}$.

Preparing $tcs_{D78S}$: the first round of PCR: the sequence of the template is given as SEQ ID NO: 4 in Sequence Listing, and primer 1 & 5 are used to produce fragment of tcs78-a; the second round of PCR: the sequence of the template is given as SEQ ID NO: 4 in Sequence Listing, and primer 2 & 6 are used to produce fragment of tcs78-b; the third round of PCR: the 1:1 mixture of tcs78-a and tcs78-b is used as PCR template, and primer 1 & 2 are used to produce $tcs_{D78S}$.

Preparing $tcs_{Y55G/D78S}$: the first round of PCR: the sequence of the template is given as SEQ ID NO: 1 in Sequence Listing, and primer 1 & 5 are used to produce fragment of tcs55/78-a; the second round of PCR: the sequence of the template is given as SEQ ID NO: in Sequence Listing, and primer 2 & 6 are used to produce fragment of tcs55/78-b; the third round of PCR: the 1:1 mixture of tcs55/78-a and tcs55/78-b is used as PCR template, and primer 1 & 2 are used to produce $tCS_{Y55G/D78S}$. (An alternative protocol: the first round of PCR: the sequence of the template is given as SEQ ID NO: 2 in Sequence Listing, and primer 1 & 3 are used to produce fragment of tcs55/78-a; the second round of PCR: the sequence of the template is given as SEQ ID NO: 2 in Sequence Listing, and primer 2 & 4 are used to produce fragment of tcs55/78-b; the third round of PCR: the 1:1 mixture of tcs55/78-a and tcs55/78-b is used as PCR template, and primer 1 & 2 are used to produce $tcs_{Y55G/D78S}$.)

The preparation method of other coding genes of the mutants is the same as that of $tcs_{Y55GS}$, $tcs_{D78S}$, or $tcs_{Y55G/D78S}$, except the use of the corresponding primers of primers 3, 4, 5 or 6.

Example 2

The Biological Activities of TCS Mutants a) Assay for the Protein Synthesis Inhibition of TCS Mutants The rabbit reticulocyte lysate in vitro translation system (Promega, Madison, Wis.) is used to determine the protein synthesis inhibiting activity of TCS mutants following the manufacturer's instruction. [$^{35}$S]methionine is from PerkinElmer Life Sciences Company. The $IC_{50}$s of TCS mutants are shown in table 1, which indicates that the $IC_{50}$ of $TCS_{D78C}$ is 20 nM<$IC_{50}$≦50 nM, the $IC_{50}$s of $TCS_{D78A}$ and $TCS_{D78A}$ are 10 nM<$IC_{50}$≦20 nM, and the $IC_{50}$s of natural TCS (nTCS, IC50=1.31×10$^{-9}$M) and other mutants are 1 nM<$IC_{50}$≦10 nM b) Assay for the Cytotoxicity of TCS Mutants on JAR Cells The JAR cells are planted in 96 microplates with the density of 1×10$^4$ cells/well, and 25 μg/ml nTCS (positive control) or TCS mutants are added into each well. The cells are cultured at 37□ for 48 hours, and the MTT assay is carried out to determine the viability of JAR cells. Furthermore, nTCS and TCS mutants are transfected into JAR cells by lipofectAMINE following Invitrogen's instruction. 48 hours later, the MTT assay is carried out to determine the viability of JAR cells. The results are shown in table 1, which indicates that when directly added into intact cells, the TCS mutants can not inhibit the growth of JAR cells, with the viability of JAR cells being over 90%. The mutants can inhibit the growth of JAR cells after cell transfection. The cell viabilities of the cells transfected with $TCS_{Y55G}$, $TCS_{Y55A}$, $TCS_{Y55L}$, $TCS_{D78S}$ and $TCS_{D78V}$ are in the range of 40% to 50%, and the cell viabilities of cells transfected with other mutants are in the range of 50% to 60%.

c) Assay for Apoptosis-Inducing Activity of TCS on JAR Cells

The ApoAlert® Caspase-3 Colorimetric Assay Kit (Clontech Co., USA) is used following the manufacturer's instruction. The cell culture and liposome transfection are the same as those in part b), and the assay is carried out 12-hour after protein treatment. The results are shown in table 1, which indicates that when directly added into intact cells, the mutants can not induce the caspase-3 activity of JAR cells (the active unit of caspase-3≦1.0), but they can do the work after transfection.

TABLE 1 the biological activities of TCS mutants

| TCS Mutants | Protein synthesis inhibition in vitro* | Cytostatic activity on JAR cells† | Cytostatic activity on JAR cells after transfection† | Ability of inducing caspase-3 activity of JAR cells‡ | Ability of inducing caspase-3 activity of JAR cells after transfection‡ |
|---|---|---|---|---|---|
| nTCS | +++ | ++ | +++ | +++ | +++ |
| Y55G | +++ | − | ++ | − | ++ |
| Y55A | +++ | − | ++ | − | ++ |
| Y55V | +++ | − | + | − | + |
| Y55L | +++ | − | ++ | − | + |
| Y55I | +++ | − | + | − | + |
| D78S | +++ | − | ++ | − | ++ |
| D78T | ++ | − | + | − | + |

TABLE 1-continued the biological activities of TCS mutants

| TCS Mutants | Protein synthesis inhibition in vitro* | Cytostatic activity on JAR cells† | Cytostatic activity on JAR cells after transfection† | Ability of inducing caspase-3 activity of JAR cells‡ | Ability of inducing caspase-3 activity of JAR cells after transfection‡ |
|---|---|---|---|---|---|
| D78N | ++ | − | ++ | − | ++ |
| D78Q | +++ | − | + | − | ++ |
| D78A | ++ | − | + | − | ++ |
| D78C | + | − | + | − | + |
| Y55G/D78S | +++ | − | + | − | ++ |

Note:
*+++: 1 nM ≤ $IC_{50}$ ≤ 10 nM; ++: 10 nM < $IC_{50}$ ≤ 20 nM; +: 20 nM < $IC_{50}$ ≤ 50 nM.
†+++: Viability ≤ 40%; ++: 40% < Viability ≤ 50%; +: 50% < viability ≤ 60%; −: ≥90%.
‡+++: ≥5.0; ++: 3.5 ≤ active unit < 5.0; +: 2.0 ≤ active unit < 3.5; −: ≤1.0.
This embodiment indicates that the mutants with single or double mutations on CTS tyrosine-55 and aspartate-78 remain the RI activity but lose the cytostatic activity on tumor cells; they show cytotoxicity and caspase-apoptosis-inducing activity, however, after liposome transfection.

Further analyses show that to remove the effect of phenyl residue, the tyrosine-55 can be mutated to other 5 aliphatic amino acids; to eliminate high hydrophilicity, the aspartate-78 can be mutated to 6 types of amino acids with the hydrophobicity of between ±1 (Asp −2.5, Ser −0.3, Thr 0.4, Asn −0.2, Gln −0.2, Gly 0, Cys 1.0; data from Nozaki-Tanford and Levitt). Because the 55-glycine and 78-serine showed the minimum effects on the protein synthesis inhibition and anti-tumor activity after transfection, the mutants of $TCS_{Y55G}$, $TCS_{D78S}$ and $TCS_{Y55G/D78S}$ are preferred.

Example 3

The Characteristics of $TCS_{Y55G}$, $TCS_{D78S}$ and $TCS_{Y55G/D78S}$

Figure 2:
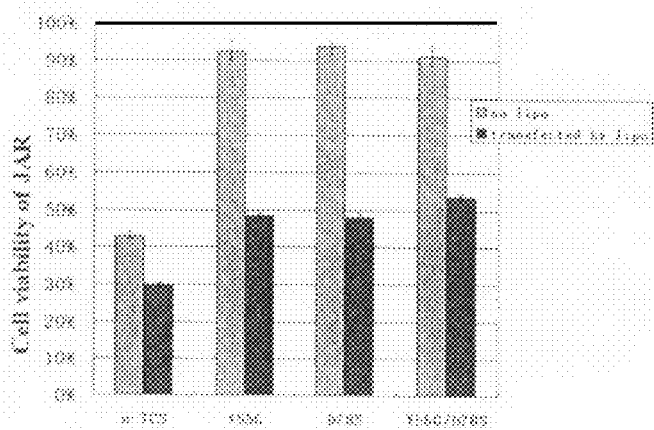
FIG. 2 is the histogram of cytostatic activity of TCS mutants $TCS_{Y55G}$, $TCS_{D78S}$ and $TCS_{Y55G/D78S}$ on JAR cells.
Figure 3:
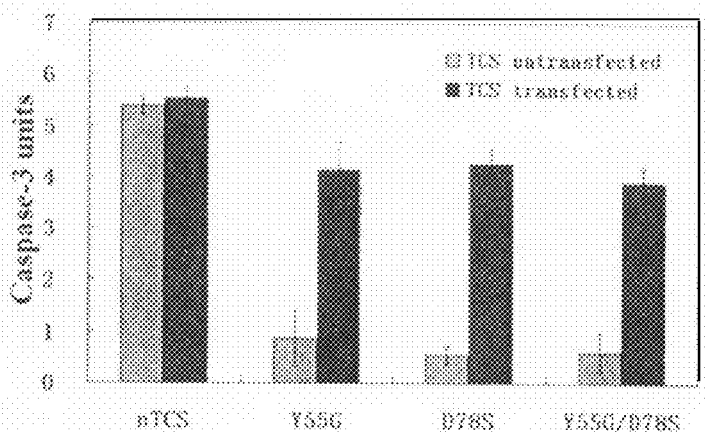
FIG. 3 is the histogram of apoptosis-inducing activity of TCS mutants $TCS_{Y55G}$, $TCS_{D78S}$ and $TCS_{Y55G/D78S}$ on JAR cells.
Figure 4:
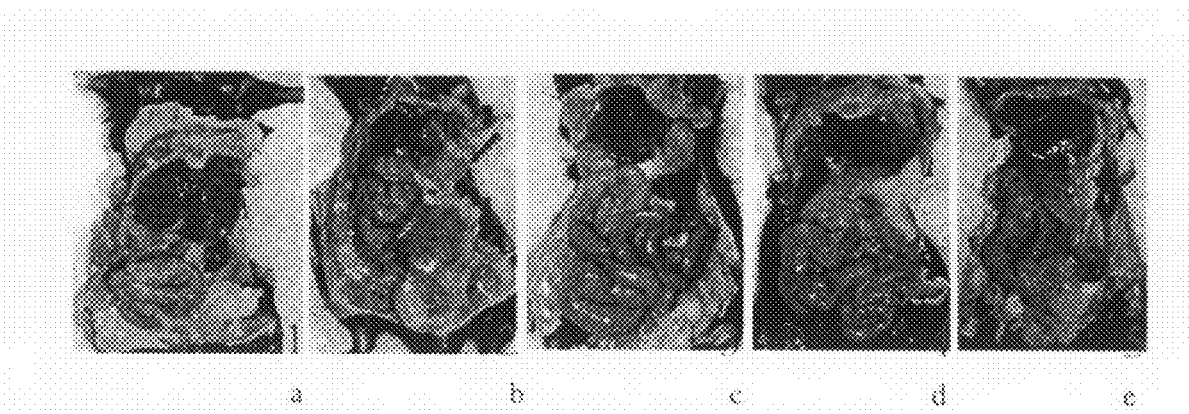
FIG. 4a is the picture showing the mice livers treated with PBS.
FIG. 4b is the picture showing the mice livers treated with nTCS.
FIG. 4c is the picture showing the mice livers treated with $TCS_{Y55G}$.
FIG. 4d is the picture showing the mice livers treated with $TCS_{D78S}$.
FIG. 4e is the picture showing the mice livers treated with $TCS_{Y55G/D78S}$.

The ability of protein synthesis inhibition of these three mutants are shown in FIG. 1, and the IC50s are $4.67 \times 10^{-9}$ M, $3.88 \times 10^{-9}$ M and $6.62 \times 10^{-9}$ M, respectively, indicating significant inhibition activities. As a comparison, the IC50 of nTCS is only $1.31 \times 10^{-9}$ M. The cytostatic activity of three mutants are shown in FIG. 2, indicating that the cell viability in nTCS group decreased to 43.1%, but the three mutants can not kill JAR cells, with the cell viability of 90.4%, 94.6% and 91.2%. However, after liposome transfection, the cell viabilities in the groups of the three mutants are 43.5%, 41.9% and 53.4% respectively. The abilities of the three mutants to induce the JAR cell apoptosis are shown in FIG. 3, showing that the three mutants can not induce JAR cell apoptosis. However, after transfection, they can induce apoptosis of JAR cells in a much greater extent comparing with the liposome control group. At the same time, the observation with phase contrast microscope shows that apoptotic body can be observed after transfection of the three mutants, which is in conformity with what has been observed in nTCS group.

Example 4

The Lowered Toxicity of TCS Mutants on Mice

15 C57BL/6j mice (about 20 g, purchased from The Animal Experimental Center of Chinese Academy of Medical Sciences) were divided into 3 groups and abdominally injected with nTCS, TCS mutants or PBS every two weeks, with the dose of 10 μg/mouse. 35 days after the administration, the mice were sacrificed and the blood is collected to detect the serum IgG and IgE levels. The mice are dissected to observe the viscera damages. The results show that the IgG and IgE levels in the groups of $TCS_{Y55G}$, $TCS_{D78S}$ and $TCS_{Y55G/D78S}$ decreased about 50% comparing to the nTCS group; and the IgG and IgE levels in the groups of $TCS_{Y55A}$, $TCS_{D78T}$, $TCS_{D78N}$ and $TCS_{D78C}$ decreased about 40%; and the IgG and IgE levels in the groups of $TCS_{Y55V}$T, $CS_{Y55L}$, $TCS_{Y55I}$, $TCS_{D78Q}$ and $TCS_{D78A}$ decreased about 30%. In viscera observation, the edge of liver lobes turned blunt, the intestines became conglutinate and the fat among organs became excrescent after treated with nTCS, whereas these symptoms were not observed in the abdominal cavity of the mice injected with mutants, especially $TCS_{Y55G}$, $TCS_{D78S}$ and $TCS_{Y55G/D78S}$ (FIG. 4a-e).

Example 5

The Amino Acid Alternation in TCS Mutants Abolishes its Cell Entry Ability

Figure 5:
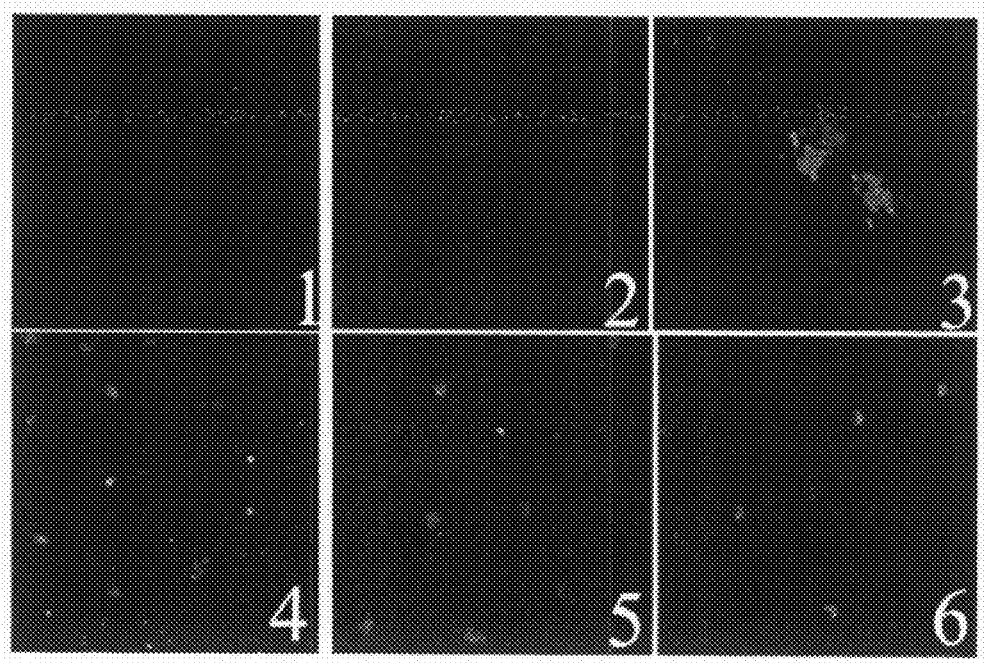
FIG. 5 is the fluorescence picture showing the ability of TCS mutants to enter JAR cells.
Figure 6:
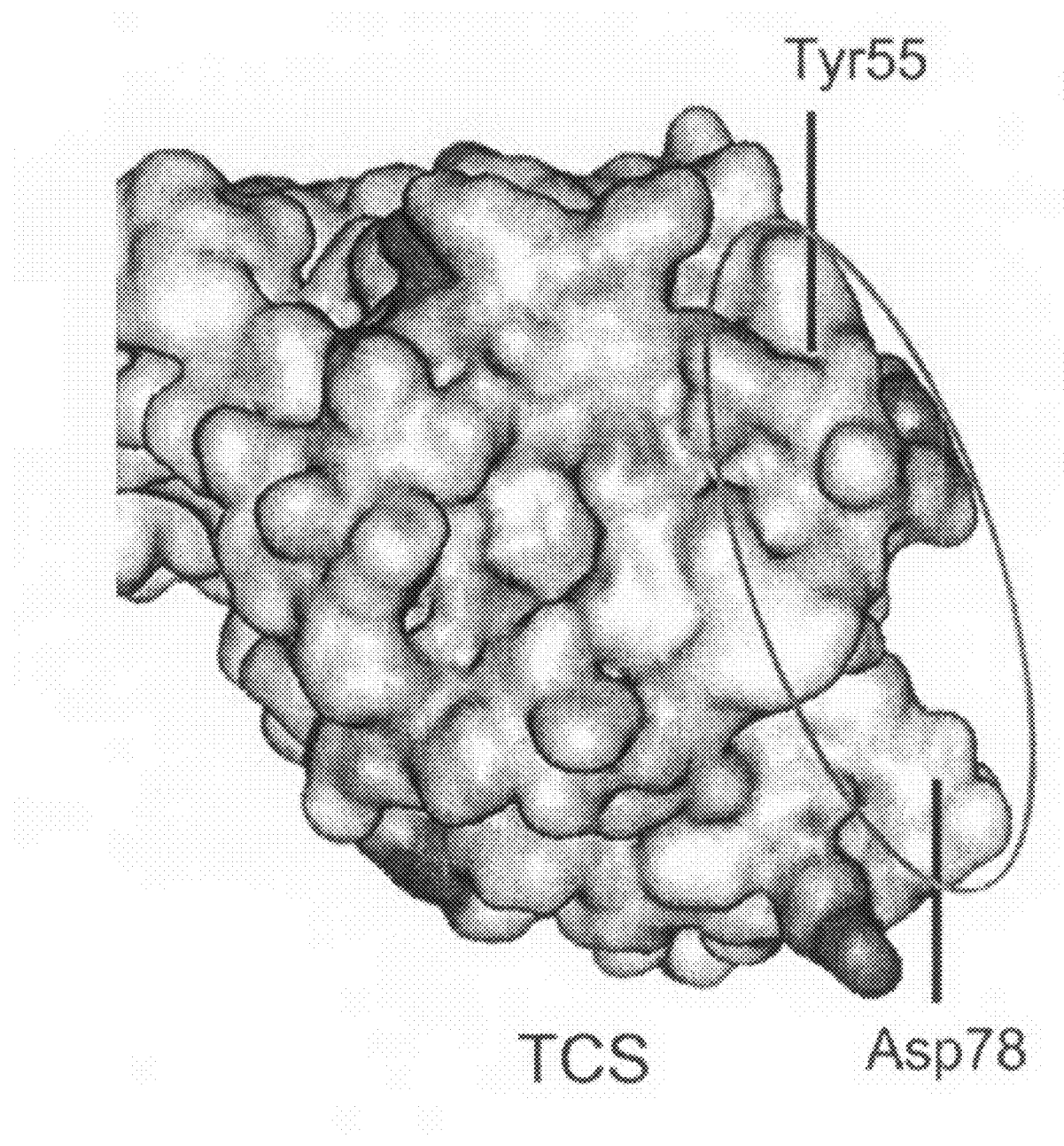
FIG. 6 is the tertiary structure of TCS and the concave domain where Y55-D78 is located.

According to the method in Example 2 part b, the FITC-labelled nTCS and mutants were added to the cultured JAR cells. After 4-12 hours, the cells were observed with fluorescence microscope. The results show that the mutants of $TCS_{Y55G}$, $TCS_{D78S}$ and $TCS_{Y55G/D78S}$ can develop faint green fluorescence on the local surface of JAR cells when they are added directly, whereas the whole cells with nTCS added show bright green fluorescence, which indicates that the mutants lose the ability to enter into cells (FIG. 5). The legends in FIG. 5: 1, untreated cells; 2, FITC-BSA treated cells; 3, FITC-nTCS treated cells; 4, FITC-$TCS_{Y55G}$ treated cells; 5, FITC-$TCS_{D78S}$ treated cells; 6, FITC-$TCS_{Y55G/D78S}$ treated cells. These data indicate that the tyrosine-55 and aspartate-78 play critical role to the cell entry of TCS, and the concave domain of 55-78 (FIG. 6) is important to the interaction with cell receptor, and the modification on this domain can cause the failure of TCS cell entry via cell receptor.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A mutant of trichosanthin, wherein at least one of the tyrosine-55 and aspartate-78 (counted from the N-terminus of trichosanthin of SEQ ID NO. 8) are mutated, with the tyrosine-55 being mutated to an aliphatic amino acid selected from the group consisting of alanine, valine, leucine, and isoleucine, and the aspartate-78 being mutated to an amino acid with low hydrophilicity.

2. The mutant of claim 1, wherein the tyrosine-55 (counted from the N-terminus of trichosanthin of SEQ ID NO. 8) is mutated to an aliphatic amino acid.

3. The mutant of claim 1, wherein the aspartate-78 (counted from the N-terminus of TCS) is mutated to an amino acid with low hydrophilicity.

4. The mutant of claim 1, wherein the tyrosine-55 (counted from the N-terminus of trichosanthin of SEQ ID NO. 8) is mutated to an aliphatic amino acid, and the aspartate-78 (counted from the N-terminus of trichosanthin of SEQ ID NO. 8) is mutated to an amino acid with low hydrophilicity.

5. The mutant as claimed in claim 4, wherein the amino acids with low hydrophilicity is serine, threonine, asparagine, glutamine, alanine, or cysteine.

6. A method of treating a subject having a carcinoma comprising administering to the subject a medicament comprising the trichosanthin of SEQ ID NO. 8 mutant of claim 1.

* * * * *